(12) United States Patent
Kawakami

(10) Patent No.: US 7,741,301 B2
(45) Date of Patent: Jun. 22, 2010

(54) TRANSPOSASE AND METHOD OF GENE MODIFICATION

(75) Inventor: Koichi Kawakami, Chiba (JP)

(73) Assignee: Japan Science and Technology Agency, Saitama (JP)

(*) Notice: Subject to any disclaimer, the term of this patent is extended or adjusted under 35 U.S.C. 154(b) by 0 days.

(21) Appl. No.: 11/375,798

(22) Filed: Mar. 14, 2006

(65) Prior Publication Data

US 2006/0212958 A1    Sep. 21, 2006

Related U.S. Application Data

(62) Division of application No. 10/148,639, filed as application No. PCT/JP00/08014 on Nov. 14, 2000, now Pat. No. 7,034,115.

(30) Foreign Application Priority Data

Dec. 3, 1999  (JP) .................. 11-345508/1999
Apr. 11, 2000 (JP) .................. 2000-109033

(51) Int. Cl.
*A01N 43/04* (2006.01)
*C07H 21/02* (2006.01)
*C12N 15/00* (2006.01)
*C12N 15/63* (2006.01)

(52) U.S. Cl. .................. 514/44; 536/23.1; 435/320.1; 435/455

(58) Field of Classification Search .................. 514/44; 536/23.1; 435/320.1, 455
See application file for complete search history.

(56) References Cited

OTHER PUBLICATIONS

Kawakami et al., Nov. 1999, GenEmbl Accession No. AB032244, pp. 1-3.*
SPTREMBL Accession Nos. Q98968, 98969, 98970, and 98971, pp. 3-4.*
Ivics et al., 1997, Cell, vol. 91, p. 501-510.*
Atkinson et al., 1993, PNAS, vol. 90, pp. 9693-9697.*
K. Kawakami et al., *Gene*, 240: 239-244 (1999).
Kawakami et al., *Gene*, 225: 17-22 (1998).
A. Koga et al., *Genbank*, Acc. No. D84375 (1999).
A. Koga et al., *FEBS Letters*, 461: 295-298 (1999).
A Koga et al., *Nature*, 383: 30 (1996).
G. Luo, *Proc. Natl. Acad. Sci. USA*, 95: 10769-10773 (1998).
L. Zhang et al., *Nucleic Acids Research*, 26 (16): 3687-3693 (1998).
A. Sherman et al, *Nature Biotechnology*, 16:1050-1053 (1998).
Z. Li et al., *Somatic Cell and Molecular Genetics*, 24(6): 363-369 (1998).
E. Rubin et al, *Proc. Natl. Acad. Sci USA*, 96: 1645-1650 (1999).
K. Kawakami et al., *Gene*, 240: 239-244 (1999), Databse accession No. AB032244 (abstract only).
A. Koga et al., *Nature*, 383: 30-30 (1996), Database accession No. Q98969 (abstract only).
Izsvak et al., *Biochemistry & Cell Biology*, 75: 507-523 (1997).
GenEmbl Accession No. AB032244, Nov. 26, 1999, pp. 1-3.
SPTREMBL Accession Nos. Q98968, 98969, 98970, 98971, 1997, pp. 3-4.
Rudinger, 1976, Peptide Hormones, Parsons, University Park Press, Baltimore. p. 1-7.
Kaye et al., 1990, Proc. Natl. Acad. Sci. USA, vol. 87, pp. 6922-6926.
Skolnick et al., 2000, Trends in Biotech, vol. 18, pp. 34-39.
De Lorenzo, Victor, "Genetic Engineering Strategies for Environmental Applications," Current Opinion in Biotechnology, 3(3): 227-231 (1992).
Lewin, B., "Genes VI", Chapter 18, p. 564 (Oxford University Press 1997) (excerpt).
Lander, E.S., et al., "Initial sequencing and analysis of the human genome", Nature, 409(6822):860-921 (2001) (excerpt).
Ivics, Z., et al., "Molecular Reconstruction of Sleeping Beauty, a Tc1-like Transposon from Fish, and Its Transposition in Human Cells", Cell, vol. 91, 501-510 (1997) (excerpt).
Kunze et al., "Transcription of transposable element *Activator (Ac) of Zea mays* L.," The EMBO Journal, vol. 6, No. 6, pp. 1555-1563 (1987).
lzsvak et al., "Short Inverted-Repeat Transposable Elements in Teleost Fish and Implications for a Mechanism of Their Amplification," Journal of Molecular Evolution, vol. 48, pp. 13-21, (January 1999).

* cited by examiner

*Primary Examiner*—Shin-Lin Chen
(74) *Attorney, Agent, or Firm*—Edwards Angell Palmer & Dodge LLP; Peter F. Corless; Mark D. Russett

(57) ABSTRACT

A transposase encoded by the Tol2 element; a polynucleotide encoding the same; a method of modifying the gene structure of a cell (preferably a vertebrate cell) by using the above protein; a method of modifying the function of a cell by modifying the gene structure thereof; and a cell having been modified in function by these methods. Also the structure of a cis element necessary in gene transfer is clarified and presented.

6 Claims, 5 Drawing Sheets

FIG. 2

```
Tol2 : 106 VDSVFPVKHVSPVTVNKAILRYIIQGLHPFSTVDLPSFKELISTLQPGISVITRPTLRSK 165
           ++ + P K+    V++ K L  II   +PF+ V+   F.E + +L+P  + +R T R
Ac   : 215 INLIEPYKYDEVVSLKKLHLA-IIMHEYPFNIVEHEYFVEFVKSLRPHFPIKSRVTARKY 273

Tol2 : 166 IAEAALIMKQKVTAAMSEVE-WIATTTDCWTA-RRKSFIGVTAHWINPG-SLERHSAALA 222
           I + L    K+K+  + +V+   +TT D WT+ + KS++ VT HWI+      L++
Ac   : 274 IMDLYLEEKEKLYGKLKDVQSRFSTTMDMWTSCQNKSYMCVTIHWIDDWCLQKRIVGFF 333

Tol2 : 223 CKRLMGSHTFEVLASAMNDIHSEYEIRDKVVCTTTDSGSNFMKAFRVFGVENNDIETEAR 282
           +G HT + L+      I  ++ I  K+   + D+ S                 N++
Ac   : 334 ---HVEGRHTGQRLSQTFTAIMVKWNIEKKLFALSLDNAS-------------ANEVAVHDI 379

Tol2 : 283 RCESDDTDSEGCGEGSDGVEFQDASRVLDQDDGFEFQLPKHQKCACHLLNLVS 335
           +  D'TDS       DG F                 H +CACH+LNLV+
Ac   : 380 IEDLQDTDSNLV---CDGAFF----------------HVRCACHILNLVA 410
```

FIG. 4
A
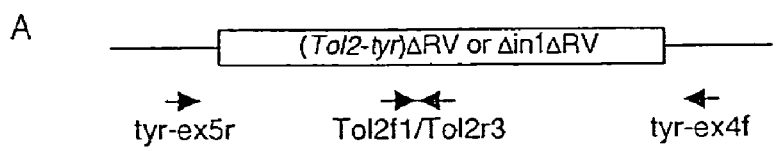
B
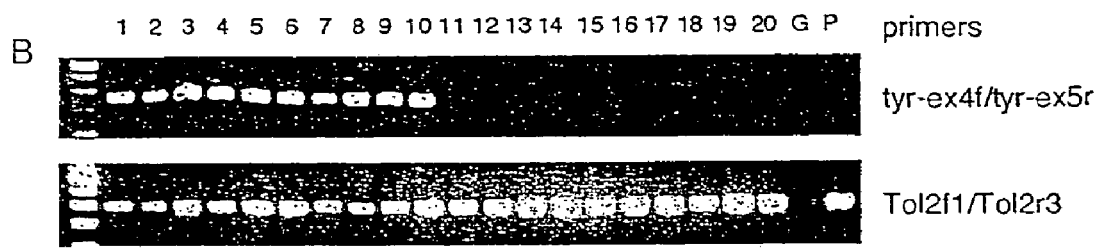
C
| | | No. of clones |
|---|---|---|
| wild type | gga gttcttga ccc | |
| plasmid | ggagttcttgacag-*Tol2*-ctggttcttgaccc | |
| excision product a | gga gttcttga ccc | 3 |
| excision product b | gga gttcttcttga ccc | 2 |
| excision product c | gga gttctcttga ccc | 1 |
D
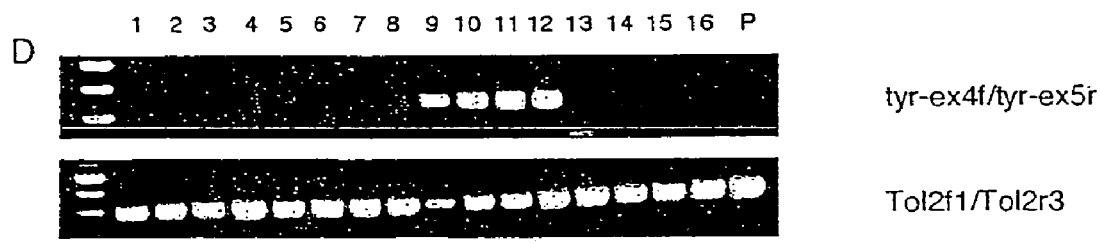

FIG. 5
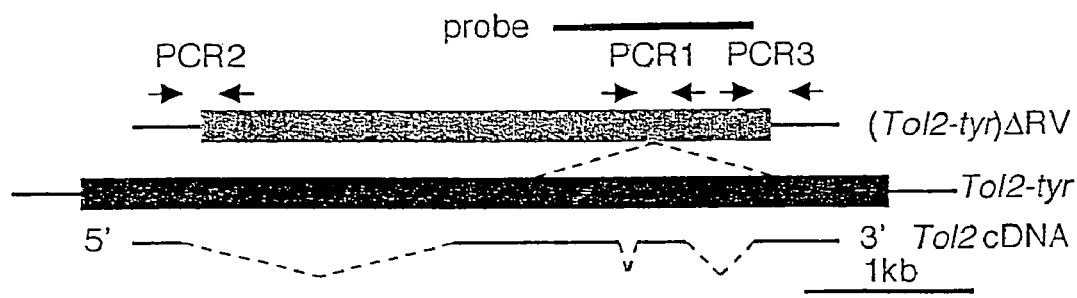
FIG. 6
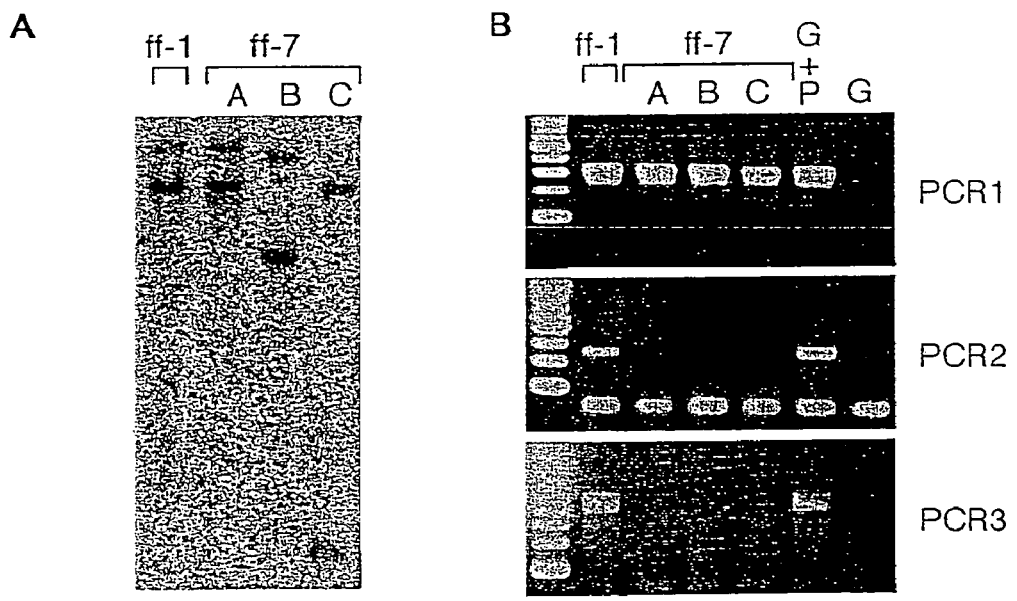
FIG. 7
A  GTTTTTTTTTTTACATCTCAACTG-Tol2-CTCAACTGATAGTCTAATCACAC
B  CGCTGAGCTCTCTTATATAGAGA-Tol2-TATAGAGATGGCTGTTATACGAG
C  AAGTGACGTCAATGTGTTTTCAG-Tol2-GTTTTCAGCTCATCTGTTCATTA

TRANSPOSASE AND METHOD OF GENE MODIFICATION

CROSS-REFERENCE TO RELATED APPLICATIONS

This application is a divisional application of U.S. application Ser. No. 10/148,639, filed Jun. 3, 2002 now U.S. Pat. NO. 7,034,115, which is a U.S. national phase application under 35 U.S.C. §371 of International Application Serial No. PCT/JP00/08014, filed Nov. 14, 2000, which claims the benefit of Japanese Application Serial No. 2000-109033, filed Apr. 11, 2000, and Japanese Application Serial No. 11-345508/1999, filed Dec. 3, 1999. The entire contents of all of the above-referenced applications are incorporated herein by this reference.

TECHNICAL FIELD

The present invention relates to a new protein having a transposase-like activity, a transposase composed of the above protein, a method of modifying the gene structure of a cellular gene by using these protein and transposase, a method of modifying the function of a cell by this method, a method of introducing a gene by this method, a plasmid used for this method, and a cell having been modified in function by this method.

BACKGROUND ART

The medaka fish (*Oryzias latipes*) is a teleost inhabiting in East Asia and has been used for studying vertebrate genetics. The mutations at the i locus of the medaka fish cause amelanotic skin and red-colored eyes. This i locus is known to encode a gene for tyrosinase. From one of the i alleles, $i^4$, DNA of about 4.7-kb was cloned and found to have a transposon-like sequence; that is to say, it included open reading frames homologous to transposases of transposons of the hAT family including hobo of *Drosophila*, Ac of maize and Tam3 of snapdragon, and short terminal inverted repeats. This medaka element was named Tol2. The laboratory strains of the medaka fish contain about 10 copies of this element per haploid genome.

In the $i^4$ mutant fish, the Tol2 element found in the tyrosinase gene locus has been shown by PCR to be excised from the target locus during embryonic development (Koga et al., 1996).

Zebrafish (*Danio rerio*), as well as the medaka fish (*Oryzias latipes*), is a small teleost and has been developed as a model animal to study vertebrate genetics and development (Takeuchi, 1966; Yamamoto, 1967; Streisinger et al., 1981). In zebrafish, large-scale chemical mutagenesis screens have been performed (Driever et al., 1996; Haffter et al., 1996), and, to facilitate cloning of the mutated genes, an insertional mutagenesis method using a pseudotyped retrovirus has been developed and performed (Lin et al., 1994; Gaiano et al., 1996; Amsterdam et al., 1997). Also, in an attempt to develop transposon technologies that would allow enhancer trap and gene trap screens to be performed, transposition of transposons of the Tc1/mariner family in fish has been tested and demonstrated (Ivics et al., 1997; Raz et al., 1997; Fadool et al., 1998). Although these results are encouraging, neither highly efficient transgenesis nor insertional mutagenesis methods using a transposon have not yet been developed.

The present inventors have been interested in developing novel transposon technologies using the Tol2 element. As a first step towards this goal, the present inventors developed a transient embryonic excision assay using zebrafish embryos, in which zebrafish fertilized eggs were injected with a plasmid DNA harboring the Tol2 element, showed that the Tol2 element was excisable from the injected plasmid DNA, and indicated that the Tol2 element is an autonomous member and is active in zebrafish (Kawakami et al., (1998) Gene 225, 17-22). Although the DNA sequence of the Tol2 element is similar to those of transposases of transposons of the hAT family, neither an active enzyme, which can function in trans, nor cis-elements essential for the excision reaction have been identified. In order to develop the Tol2 element as a useful tool for transgenesis and insertional mutagenesis, it is necessary to dissect and characterize cis and trans requirements. The functional transposase encoded by the Tol2 element had not yet been identified prior to the present invention.

DISCLOSURE OF THE INVENTION

The present invention first aims to identify mRNA transcribed from the Tol2 element injected in zebrafish embryos. Secondly, in order to determine whether the transcript encodes an active enzyme or not, the present invention develops a novel assay method, in which zebrafish fertilized eggs are co-injected with RNA synthesized in vitro using the Tol2 cDNA as a template and a plasmid DNA harboring a nonautonomous Tol2 element, which has a deletion in the transposase coding region.

The present invention also identifies the active trans-factor and essential cis-elements, that function in excision of the Tol2 element in zebrafish.

Consequently, the present invention results in a new protein encoded by the Tol2 element and a polynucleotide encoding the same. Also the present invention, by using the above protein, results in a method of modifying the gene structure of a cell, preferably the gene structure of a vertebrate, in a method of modifying the function of a cell by modifying the gene structure thereof, and in a cell having been modified in function by these methods. Furthermore, the present invention discloses the cis-element structures essential for transposition, and presents the same.

The present invention relates to a protein having the transposase-like activity, which has an amino acid sequence shown in SEQ ID NO:2, an optionally substituted amino acid sequence with any replacements or deletions in part of the original amino acid sequence, or an optionally substituted amino acid sequence with addition of other amino acids to the original amino acid sequence. Also the present invention relates to a transposase comprising the said protein.

Further, the present invention relates to the nucleic acid encoding the said protein, wherein the nucleic acid is preferably DNA having a nucleotide sequence shown in SEQ ID NO:1 or DNA which can hybridize to the said DNA, or is the corresponding RNA.

The present invention reveals that the said protein has a transposase-like activity which catalyzes transposition of the above transposon, and relates to a method of modifying the gene structure comprises the excision in part of a gene in a cell, preferably a vertebrate cell, or the insertion of the excised part into any other locus in the presence of the said protein or the nucleic acid which can produce the said protein. It is preferable that the said excised gene has nucleotide sequences containing at least one inverted repeat (the Angel elements) in forepart of its nucleotide sequence.

Further, the present invention relates to a method of inserting a foreign gene into a gene of a cell, and a method of modifying a function of a cell based on gene expression, and furthermore relates to a cell having been modified in function by the said method.

Also, the present invention relates to a plasmid used in these methods and, more in detail, a plasmid which contains DNA having a nucleotide sequence that includes at least one inverted repeat sequence in the forepart of its nucleotide sequence.

Furthermore, in a method of inserting any DNA into the genomic DNA of a vertebrate, the present invention relates to a method of inserting any DNA into the genomic DNA of a vertebrate which is characterized by operating the said insertion of DNA autonomously using the transposase activity, wherein a preferable DNA is the Tol2 element and the vertebrate is fish.

BRIEF DESCRIPTION OF THE DRAWINGS

FIG. 2 shows a comparison of amino acid sequences of transposases of the Tol2 element described in the present invention (residues 106-335 of SEQ ID NO:2) and the Ac element (SEQ ID NO:3).

FIG. 4 shows photos, substitutes for drawings, which show the results of the PCR analysis of the excision reaction in zebrafish embryos described in the present invention (SEQ ID NOs:4-9, respectively in order of appearance).

FIG. 5 shows the structures of the (Tol2-tyr)ΔRV plasmid used for transposition of the Tol2 element into the genome, the Tol2-tyr plasmid and Tol2 cDNA. The black line in the upper part of FIG. 5 shows the probe used for Southern blot analysis.

FIG. 6 shows photos, substitutes for drawings, which show the results of Southern blot analysis of F1 progeny fish from each parental fish (ff-1 and ff-7), wherein the presence of Tol2 is identified (FIG. 6, A) and show the results of PCR (FIG. 6, B).

FIG. 7 shows the nucleotide sequences surrounding the Tol2 element inserted in the genome of F1 progeny A (left: SEQ ID NO:10; right: SEQ ID NO:11), B (left: SEQ ID NO:12; right: SEQ ID NO:13) and C (left: SEQ ID NO:14; right: SEQ ID NO:15) from ff-7.

BEST MODE FOR CARRYING OUT THE INVENTION

Previously, the present inventors injected the Tol2-tyr plasmid, a plasmid harboring the Tol2 element cloned from the tyrosinase gene locus, into zebrafish fertilized eggs and showed that the Tol2 element is excisable from the injected plasmid DNA (Kawakami et al., 1998). In order to identify a transcript encoding a putative transposase activity, total RNA from embryos injected with the Tol2-tyr plasmid were prepared. The present inventors first performed 3' RACE using four pairs of nested primers that annealed different parts of the Tol2 sequence.

Nested forward primers used to perform 3' RACE are:

```
                                      (SEQ ID NO:16)
   Tol2f2;  5'-TTGGTCAGACATGTTCATTG-3'
   and
                                      (SEQ ID NO:17)
   Tol2f3;  5'-ATGTTCATTGGTCCTTTGGA-3', (SEQ ID NO:18)
   Tol2f4;  5'-ATAGCTGAAGCTGCTCTGATC-3'
   and
                                      (SEQ ID NO:19)
   Tol2f5;  5'-CTGCTCTGATC ATGAACAG-3', (SEQ ID NO:20)
   Tol2f8;  5'-GCTTAATAAAGAAATATCGGCC-3'
   and
                                      (SEQ ID NO:21)
   Tol2f9;  5'-AATATCGGCCTTCAAAAGTTCG-3', (SEQ ID NO:22)
   Tol2f12; 5'-CTGTAATCAGAGAGTGTATGTGTA-3'
   and
                                      (SEQ ID NO:23)
   Tol2f13; 5'-ATTGTTACATTTATTGCATACAAT-3'.
``` cDNAs with polyadenylation were successfully amplified by 3' RACE using Tol2f8 and Tol2f9, and Tol2f4 and Tol2f5, but not by 3' RACE using Tol2f2 and Tol2f3, and Tol2f12 and Tol2f13.

Then, using nested reverse primers designed to perform 5' RACE,

```
                                      (SEQ ID NO:24)
   Tol2r4;  5'-CTCAATATGCTTCCTTAGG -3' and (SEQ ID NO:25)
   Tol2r5;  5'-CTTCCTTAGGTTTGATGGCG-3',
```

Figure 1:
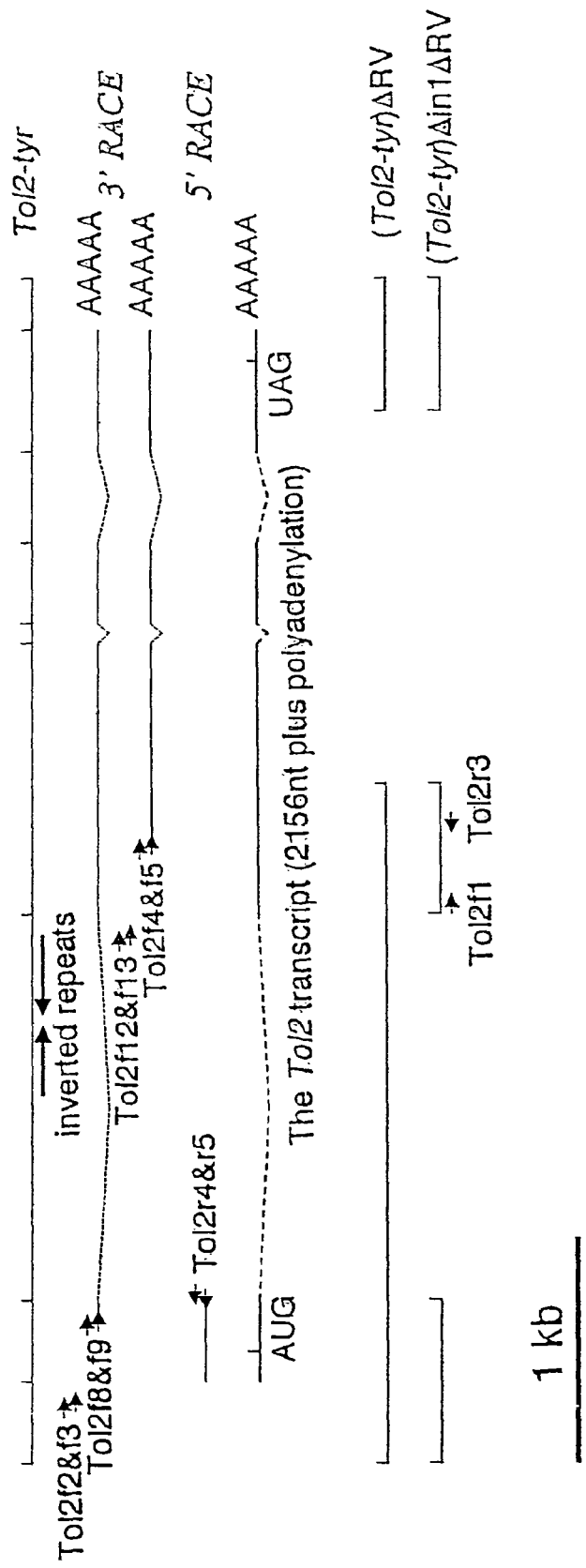
FIG. 1 shows the structure of the Tol2 plasmid and the transcript, and the structure of cDNAs described in the present invention. The dotted lines indicate introns. The inverted repeat (the Angel elements) in the first intron and positions of primers used in the present invention are shown by arrows.

5' RACE was performed and the full-length Tol2 transcript of 2156 nucleotides was identified (FIG. 1).

The cDNA sequence obtained is shown in SEQ ID NO:1.

FIG. 1 shows the structures of the Tol2 plasmids and its transcript. The top line of FIG. 1 shows the full-length Tol2 (Tol2-tyr). Dotted lines in the figure show introns. The inverted repeat (the Angel elements) in the first intron and positions of the said primers are shown by arrows. The lower three lines of FIG. 1 show the results of 3' RACE and 5' RACE. In each case, introns are shown as dotted lines.

The fifth line shows the structure of the full-length mRNA. The translated region corresponds to the nucleotide sequence between the 85th (ATG) and the 2032nd nucleotide (TAG) of cDNA of sequence number 1.

The two lines in the bottom show the structures of deletion mutants, (Tol2-tyr)ΔRV, and (Tol2-tyr) Δin1ΔRV.

In the 5' RACE analysis, aberrant transcripts that started from the plasmid sequence and jumped into cryptic splice acceptor sites in the first exon of the Tol2 element were also found (data not shown). These transcripts were not studied further.

DNA sequencing of the cDNA revealed the exon-intron structure of the Tol2 element (i.e., four exons and three introns) (as shown in the upper part of FIG. 1). The cDNA encodes a protein of 649 amino acids. The amino acid sequence of this protein is shown in SEQ ID NO:2.

Although the Tol2 element had been known to have a transposon-like sequence, the present invention for the first time identified that the Tol2 element encodes a protein and the expression of the protein described here generates the function. That is to say, the present invention results in a new protein encoded by the Tol2 element and also a polynucleotide which encodes the protein described here.

FIG. 2 shows a comparison of amino acid sequences of the protein described in the present invention and a known transposase of a transposon of the hAT family. This comparison shows these proteins are similar, especially in the middle part (FIG. 2). But the amino acid sequences of $NH_2$— and COOH-terminus rather varies.

In order to determine whether the protein (the Tol2 transcript) identified in the present invention encodes a functional enzyme, a new transient embryonic excision assay by co-injection was developed and, by using this method, identification of the enzymatic activity was performed.

Zebrafish fertilized eggs were co-injected with mRNA synthesized in vitro using the cDNA shown in the sequence number 1 as a template and the (Tol2-tyr)ΔRV plasmid containing (Tol2-tyr)ΔRV (see FIG. 1), which has a deletion of the nucleotides between the EcoRV sites of the Tol2 element. About 8 hours after the co-injection, DNA was prepared from each embryo and analyzed by PCR using primers, tyr-ex4 f and tyr-ex5r,

```
                                          (SEQ ID NO:26)
tyr-ex4f:  5'-GCTACTACATGGTGCCATTCCT-3'

Figure 3:
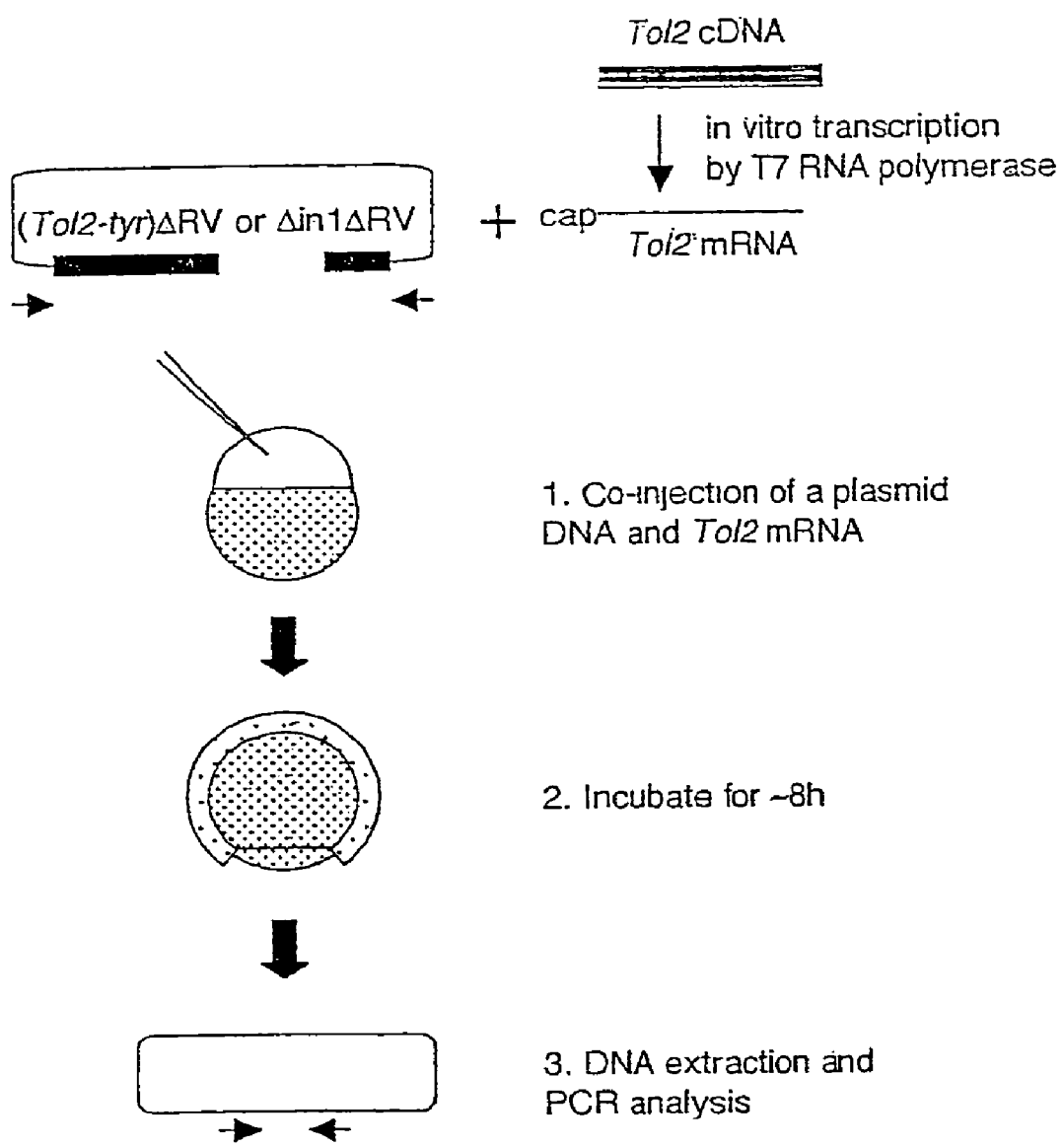
FIG. 3 shows a scheme for the transient embryonic excision assay by co-injection described in the present invention. Primers (tyr-ex4f and tyr-ex5r) used to detect the excision products are shown by arrows.

(SEQ ID NO:27)
tyr-ex5r:  5'-CACTGCCAGATCTGCTGGGCTT-3'
``` which were prepared based on the sequence adjacent to the Tol2 element. FIG. 3 shows a scheme of this method and these primers are shown in FIG. 4A.

PCR products of about 250 bp, indicative of excision of the Tol2 element from (Tol2-tyr)ΔRV plasmid, was amplified in all embryos analyzed (56 out of 56, see FIG. 4B lanes 1-10). This PCR product was never detected from embryos injected only with the (Tol2-tyr)ΔRV plasmid DNA (0 out of more than 50, see FIG. 4B lanes 11-20).

The PCR products from six different embryos were cloned and sequenced. Three of them had the wild-type medaka fish tyrosinase gene sequence (FIG. 4C, excision product a), indicating that precise excision had occurred, and the other three had nearly wild type sequences with addition of a few nucleotides (FIG. 4C, excision products b and c), characteristic to excision of transposons of the hAT family (Pohlman et al., 1984; Sutton et al., 1984; Koga et al., 1996; Kawakami et al., 1998), suggesting that the excision event in this experiment is catalyzed by a transposase-like activity.

These results, i.e., when co-injected with the mRNA which has the nucleotide sequence shown in sequence number 1 of the present invention, the PCR product characteristic to excision of the transposon was obtained and, when co-injected without the mRNA, such PCR products were not obtained, indicate that the protein (the Tol2 transcript) described in the present invention encodes a functional transposase, which can catalyze the excision. Further, these results show that the (Tol2-tyr)ΔRV plasmid contains sequences of cis-elements essential for the excision.

FIG. 4 shows the results of this experiment and arrows in FIG. 4A show positions and directions of the primers used in the analyses. The upper panel of FIG. 4B is a photo, a substitute for a drawing, which shows the PCR products using primers tyr-ex4f and tyr-ex5r, and the lower panel shows the PCR products using primers Tol2f1 and Tol2r3. In lanes 1-10, zebrafish embryos were injected with both the (Tol2-tyr)ΔRV plasmid and the Tol2 mRNA, in lanes 11-20 the (Tol2-tyr) ΔRV plasmid alone was injected, and in lane G and P PCR products were amplified from 50 ng of the zebrafish genomic DNA and from 10 pg of the (Tol2-tyr)ΔRV plasmid DNA. FIG. 4C shows the DNA sequences of the excision products obtained in the above experiments. The Tol2 sequence is shown in bold and 8 bp direct repeat sequences flanking to the Tol2 element are underlined.

It was noted that, although the excision products could be detected after a single-round PCR amplification in the experiments in the present invention, two rounds of PCR were required in the previous analysis, in which fertilized eggs were injected with a sole plasmid DNA containing the full-length Tol2 element without mRNA prepared in vitro. The higher efficiencies of the excision reaction observed here can be explained as more transposases were supplied by RNA injection than those supplied by DNA injection.

The first intron of the Tol2 element contains about 300 bp of large inverted repeats, and the repeat was recently identified as the Angel element (Izsvak et al., 1999) (see FIG. 1). To test whether the sequence in the intron is essential for excision, we constructed the (Tol2-tyr) Δin1ΔRV plasmid, containing (Tol2-tyr) Δin1ΔRV (see the bottom of FIG. 1), which completely lacked the sequences of the first intron, and its activity was analyzed by co-injection with the Tol2 mRNA as the said method. This result is shown in FIG. 4D.

The upper panel of FIG. 4D is a photo, a substitute for a drawing, which shows PCR products amplified using primers tyr-ex4f and tyr-ex5r and, the lower panel shows PCR products amplified using primers Tol2f1 and Tol2r3. In lanes 1-8, zebrafish embryos were injected with both the (Tol2-tyr) Δin1ΔRV plasmid and the Tol2 mRNA, in lanes 9-12 both the (Tol2-tyr)ΔRV plasmid and the Tol2 mRNA were injected, and, in lanes 13-16, the (Tol2-tyr) Δin1ΔRV plasmid alone was injected. Lane P shows the PCR product amplified from 10pg of the (Tol2-tyr) Δin1ΔRV plasmid DNA.

In lanes 9-12, the said experiment was conducted as controls and the PCR products indicating the excision could be detected, but the excision product could not be detected in lanes 1-8 when the plasmid lacking the intron part (0 out of 16, see FIG. 4D lanes 1-8) was used, suggesting that the first intron contains cis-elements essential for excision.

Further, the (Tol2-tyr) Δin1 plasmid, containing (Tol2-tyr) Δin1 which restored theΔRV deletion and was about the same size as the (Tol2-tyr) ΔRV plasmid, i.e., which has a deletion between the 644th and 2163rd nucleotides of the Tol2 element, was also examined by the co-injection assay, but PCR product indicating the excision could not be obtained (0 out of 16, data not shown).

Although, further analyses using smaller deletions and point mutations in the first intron sequence will be needed to define the essential cis-sequences for excision precisely, since these results show that the intron part is essential for the excision and the intron contains the Angel elments as inverted repeats, it can be thought that the inverted repeats are essential sequences for the excision described in the present invention.

Thus, we successfully identified for the first time the transcript (the protein described in the present invention) encoded by the Tol2 element and also identified a transposase activity of this protein and cis-sequences essential for transposition. These discoveries will lead to a biochemical characterization of the Tol2 transposase.

On the other hand, transposition of transposons belonging to the Tc1/mariner family into the zebrafish genome has been reported (Raz et al., 1997; Fadool et al., 1998). In the experiments described in their reports, zebrafish one-cell-stage embryos were co-injected with transposase RNA transcribed in vitro and transposon vectors containing essential cis-sequences.

While a transposon belonging to a different family may have different specificities and efficiencies for insertion into the genome, by a method of present invention which is a novel transposon technology in fish using the Tol2 element, since its transposon excision procedure has been carried out in the way of Raz et al., it might be possible to transpose DNA such as the Tol2 element into the genome in the way conducted by using transposons of the Tc1/mariner family.

Therefore, we tested whether the Tol2 element can be inserted into the zebrafish genome by transposition. It is known that the zebrafish genome does not contain the Tol2 element.

To test whether the Tol2 element encodes a transposase that can catalyze transposition, zebrafish fertilized eggs were co-injected with RNA transcribed in vitro using the Tol2 cDNA as a template, which encoded a putative transposase, and a plasmid DNA harboring the (Tol2-tyr)ΔRV element, which has a deletion in part of the region presumed to code the transposase.

The structures of (Tol2-tyr)ΔRV plasmid and Tol2 cDNA are shown in FIG. 5. 3' and 5' indicate the direction of transcription.

The injected eggs were raised to adulthood and mated to non-injected fish. And the progeny fish were analyzed for the presence of theTol2 sequence.

Two out of eight injected fish could transmit the Tol2 sequence to their progeny. These two fishes were named ff-1 (founder fish-1) and ff-7 (founder fish-7).

Two fish out of 68 F1 fish from the ff-1 fish had the Tol2 sequence. These two fish had the sequence of the plasmid portion as well as the Tol2 sequence. On the other hand, 25 fish out of 50 F1 fish from the ff-7 fish had the Tol2 sequence. These 25 fish did not have the plasmid sequence and were classified into three groups, A, B and C, from the result of Southern blot shown in FIG. 6A. 7 fish were grouped as A, 3 fish as B, and 15 fish as C.

FIG. 6A is a photo, a substitute for a drawing, which shows the result of Southern blot analysis using a probe shown in FIG. 5, in which DNA samples prepared from caudal fins of F1 fish from ff-1and ff-7 were digested with EcoRV. Two samples from ff-1 showed the same pattern but samples from ff-7 showed three patterns, A, B and C.

Then, PCR analyses of F1 fish from ff-1 and ff-7 were performed. Primers used were shown in FIG. 5 as PCR1, PCR2 and PCR3. As controls, zebrafish genomic DNA (G) and genomic DNA plus (Tol2-tyr)ΔRV plasmid DNA (G+P) were used. In F1 fish from ff-7, PCR products using PCR2 and PCR3 could not be amplified. This indicated that progeny fish from ff-7, unlike progeny fish from ff-1, did not have the plasmid sequence flanking to the Tol2 element.

From the ff-7 progeny fish, DNA fragments containing the Tol2 sequence and the flanking region were cloned by inverse PCR and sequenced. In each three case, A, B and C, the Tol2 sequence was surrounded by zebrafish genomic sequences and 8 bp duplications were created adjacent to the insertion. 8 bp duplications at both ends of the Tol2 element are characteristic to integration of transposons of the hAT family, indicating that the integration described here was catalyzed by a transposase.

FIG. 7 shows the determined nucleotide sequences of three types, A, B and C. Tol2 in FIG. 7 shows the Tol2 sequence. In A repeats of [CTCAACTG], in B repeats of [TATAGAGA], and in C repeats of [GTTTTCAG] were created at both ends of and adjacent to the Tol2 sequence.

In the vertebrate cultured cells and the germ line, transposition activities of Sleeping Beauty which was reconstituted and activated artificially (Ivics, Z., et al., Cell, 91, 501-510 (1977)), Tc3 of *C. elegans* (Raz, E., et al., Current Biology, 8, 82-88 (1977)) and mariner of *Drosophila* (Fadool, J. M., et al., Proc. Natl. Acad. Sci. USA, 95, 5182-5186(1988)), all belonging to the Tc1/mariner family, have been reported. No autonomous transposon activity residing endogenously in any vertebrate genome, however, has been reported.

The present invention is the first report that identified an autonomous element from a vertebrate genome and also for the first time reported a functional transposase activity in vertebrate.

Therefore, the present invention relates not only to a method to excise a gene autonomously in vertebrate but also to a method to insert the excised gene into any locus or any gene on the genome.

The protein in the present invention has the amino acid sequence shown in SEQ ID NO:2, but all of the amino acids shown there are not necessarily required, and the protein in the present invention can include a protein having the transposase activity described in the present invention or similar activities described above (both of these are called transposase-like activities) and also can include a protein having replacement or deletion in part of amino acids of the above protein, or having addition of any other amino acids to the above protein. And preferably it has the amino acid sequence derived from the Tol2 element. Further, the protein in the present invention includes a protein which is produced from mRNA having the nucleotide sequence corresponding to SEQ ID NO:1.

The nucleic acid in the present invention encodes the amino acid sequence which is related to the said protein, and preferably which has the polynucleotide having the sequence shown in SEQ ID NO:1. The nucleic acid in the present invention includes not only the said nucleotide sequence but also a nucleotide sequence which can hybridize to the said nucleic acid, preferably under stringent conditions.

As for a method of modifying the gene structure of a gene in a cell in the presence of the protein in the present invention or the nucleic acid which can produce the said protein, by introducing the protein or the nucleic acid, for instance the mRNA which can produce the protein described here, and, at the same time, by introducing genes including a gene to be transposed, for instance a plasmid, the gene structure in a cell can be modified by the enzymatic activity of the protein in the present invention. The modification in the present invention is involved preferably in autonomous transposition. The cell is preferably an animal cell, more preferably a vertebrate cell, and much more preferably fish cell including a zebrafish cell.

Genes containing the said gene to be transposed can be substances which do not exist in a natural cell, such as a plasmid carrying a foreign gene to be transposed, and also can be a genomic gene existing in a natural cell. In this case, cis-elements required for transposition could be added to the gene if necessary. The gene to be transposed is preferably a transposon, in certain circumstances, it may be a gene that insert a normal gene into the cell which has a disease caused by abnormalities of genes of various kinds.

Further, a method of modification in the present invention may only include the excision of part of a gene in a cell such as an inserted plasmid, however, may also include the insertion of all or part of the gene excised by this method, into any gene.

A gene excised in a method of modification in the present invention preferably has nucleotide sequences containing at least one inverted repeat in the forepart of its nucleotide sequence. The inverted repeat is thought as a cis-element or part of cis-elments for transposition of the gene.

Further, the present invention, by using the said methods of modification, relates to a method of introducing a foreign gene into a gene of a cell and to a method of modifying a function of a cell based on expression of the gene. By performing the said methods, for example, it is possible for a foreign gene on a plasmid to be transposed into the genome in a cell, and for a new gene, which the cell concerned does not contain originally, to be inserted into a cell. Further, by expression of the newly inserted gene, it is possible to modify a function of a cell. Furthermore, the present invention can result in a cell, whose function has been modified by this method. The said cell is preferable as a cell described in this method.

As a plasmid in the present invention which contains the nucleotide sequence having at least one inverted repeat in the forepart of its nucleotide sequence, an optional substitute is to mediate transposition of a gene therein, contains a region containing at least one inverted repeat and a gene to be transposed near the repeat, and is easy to be inserted into a cell.

EXAMPLES

The present invention will be described by Examples below more precisely, but these Examples do not limit the present invention.

In the experiments in the present invention, eggs for injection were obtained from zebrafish strains, Tuebingen, TL and brass and were used for the following experiments.

Example 1

Cloning of cDNA

Zebrafish fertilized eggs were injected with the (Tol2-tyr) plasmid and, 9 hours after the injection, total RNA was extracted from 50 of zebrafish embryos with Tri Zol Reagent (Life Technologies, Inc.) and about 3 µg of the total RNA obtained was used for 3' RACE and 5' RACE, respectively.

Nested forward primers used to perform 3' RACE are:

```
                                         (SEQ ID NO:16)
Tol2f2;  5'-TTGGTCAGACATGTTCATTG-3'
and
                                         (SEQ ID NO:17)
Tol2f3;  5'-ATGTTCATTGGTCCTTTGGA-3', (SEQ ID NO:18)
Tol2f4;  5'-ATAGCTGAAGCTGCTCTGATC-3'
and
                                         (SEQ ID NO:19)
Tol2f5;  5'-CTGCTCTGATC ATGAAACAG-3', (SEQ ID NO:20)
Tol2f8;  5'-GCTTAATAAAGAAATATCGGCC-3'
and
                                         (SEQ ID NO:21)
Tol2f9;  5'-AATATCGGCCTTCAAAAGTTCG-3',
and
                                         (SEQ ID NO:22)
Tol2f12; 5'-CTGTAATCAGAGAGTGTATGTGTA-3'
and
                                         (SEQ ID NO:23)
Tol2f13; 5'-ATTGTTACATTTATTGCATACAAT-3'.
```

Nested reverse primers used for 5' RACE are:

```
Tol2r4;  5'-CTCAATATGCTTCCTTAGG-3'       (SEQ ID NO:24)
and
Tol2r5;  5'-CTTCCTTAGGTTTGATGGCG-3'.     (SEQ ID NO:25)
```

The 3' RACE and 5' RACE products were gel-extracted, cloned with TOPO TA Cloning Kit (Invitrogen, Inc.) and sequenced using the ABI PRISM 310 Genetic Analyzer.

The sequence determined is shown in SEQ ID NO:1 and the amino acid sequence of its translated region is shown in SEQ ID NO:2.

Also, the summary is shown in FIG. 1. The numbers in the parentheses are bp from the 5' end of the Tol2 element. DDBJ/EMBL/Genbank accession number for the cDNA sequence is AB032244.

Example 2

Construction of the (Tol2-tyr) Δin1ΔRV plasmid

The (Tol2-tyr)Δin1Δplasmid was first constructed by replacing the NruI-NspV of the (Tol2-tyr) plasmid with the NruI-NspV fragment of the cDNA and the resulting plasmid was digested with EcoRV and self-ligated.

Example 3 mRNA Synthesis, Injection to Embryos and PCR Analysis

The cDNA encoding the entire coding region of the transposase was cloned in pBluescript SK+(Stratagene), linearized, digested with proteinase K and phenol/chloroform extracted. mRNA was generated by in vitro transcription by using T7 RNA polymerase and the mCAP mRNA Capping kit (Stratagene). The concentration and the size of the transcript were examined on agarose gel electrophoresis.

Zebrafish fertilized eggs were injected with 1-2 nl of a DNA solution (~25 ng/µl of a plasmid DNA) with or without the mRNA (~5 ng/µl of theTol2 mRNA) and incubated at 28° C. for ~8 hours. Each embryo was soaked in 50 µl of 10 mM EDTA, 10 mM Tris-HCl (pH8.0), 200 µg/ml proteinase K and incubated at 50° C. for 3 hours.

Then 1 µl of the lysed embryo was used for PCR (35 cycles of 94° C. 30 sec, 55° C. 30 sec and 72° C. 30 sec) using tyr-ex4f and tyr-ex5r primers (Kawakami et al., 1998). The PCR products were analyzed on 2% agarose gel electrophoresis. The result is shown in FIG. 4.

For the DNA sequencing analysis, the PCR products were gel-extracted, cloned with TOPO TA Cloning (Invitrogen) and sequenced. The presence of the injected plasmid DNA in each sample was verified by PCR (25 cycles of 94° C. 30 sec, 55° C. 30 sec and 72° C. 30 sec) using Tol2f1 (5'-TCCAC-CCATGCTTCCAGCAGTA-3', SEQ ID NO:28) and Tol2r3 (5'-CGTTGTGGTTGCAATCCATTCAAC-3', SEQ ID NO:29) primers.

INDUSTRIAL APPLICABILITY

The present invention results in a new protein having a transposase-like activity of a gene and the nucleic acid encoding the same.

Further, the present invention discloses that a transposase of a different family is able to generate an enzymatic activity which can catalyze transposition of a gene in a vertebrate cell, and greatly contributes to the development of technologies concerning the transposition of a gene in vertebrate and the analyses of mutants generated by the said transposition. On the other hand however, since recent gene technologies are extending from modification of a cell to modification of an organism, a method of transposition of a gene in a cell in the present invention is expected not to be limited only to the modification of a cell but also applicable to modification of the structures and functions of genes of mammals in the medical and agricultural fields as one of the methods for modifying the organism of the traits. It can be expected to be a powerful method especially for the gene therapy and the improvement of fish breeding.

What is claimed is:

1. A method for modifying a genome structure of a cell, the method comprising a) introducing a nucleic acid encoding a protein having the amino acid sequence of SEQ ID NO: 2, and a polynucleotide sequence comprising an exogenous nucleic acid and a cis-element of Oryzias Latipes Tol2 element into the cell; b) producing the protein in the cell; and c) modifying the genome structure by the insertion of the exogenous nucleic acid into the genome.

2. The method according to claim 1, wherein the nucleic acid encoding the protein is mRNA.

3. The method according to claim 1, wherein the cell is a vertebrate cell.

4. The method according to claim 1, wherein the exogenous nucleic acid and the cis-element of Oryzias Latipes Tol2 element are contained in a plasmid.

5. The method according to claim 1, wherein the nucleic acid encoding the protein and the polynucleotide sequence of step a) are separately introduced into the cell.

6. The method according to claim 1, wherein the nucleic acid encoding the protein and the polynucleotide sequence of step a) are simultaneously introduced into the cell.

* * * * *

SEQUENCE LISTING

<160> NUMBER OF SEQ ID NOS: 29

<210> SEQ ID NO 1
<211> LENGTH: 2156
<212> TYPE: DNA
<213> ORGANISM: Oryzias latipes

<400> SEQUENCE: 1

```
acgtcatgtc acatctatta ccacaatgca cagcaccttg acctggaaat tagggaaatt    60
ataacagtca atcagtggaa gaaaatggag gaagtatgtg attcatcagc agctgcgagc   120
agcacagtcc aaaatcagcc acaggatcaa gagcacccgt ggccgtatct tcgcgaattc   180
ttttctttaa gtggtgtaaa taagattca ttcaagatga aatgtgtcct ctgtctcccg   240
cttaataaag aaatatcggc cttcaaaagt tcgccatcaa acctaaggaa gcatattgag   300
agaatgcacc caaattacct caaaaactac tctaaattga cagcacagaa gagaaagatc   360
gggacctcca cccatgcttc cagcagtaag caactgaaag ttgactcagt tttcccagtc   420
aaacatgtgt ctccagtcac tgtgaacaaa gctatattaa ggtacatcat tcaaggactt   480
catcctttca gcactgttga tctgccatca tttaaagagc tgattagtac actgcagcct   540
ggcatttctg tcattacaag gcctacttta cgctccaaga tagctgaagc tgctctgatc   600
atgaaacaga aagtgactgc tgccatgagt gaagttgaat ggattgcaac cacaacggat   660
tgttggactg cacgtagaaa gtcattcatt ggtgtaactg ctcactggat caaccctgga   720
agtcttgaaa gacattccgc tgcacttgcc tgcaaaagat taatgggctc tcatactttt   780
gaggtactgg ccagtgccat gaatgatatc cactcagagt atgaaatacg tgacaaggtt   840
gtttgcacaa ccacagacag tggttccaac tttatgaagg ctttcagagt ttttggtgtg   900
gaaaacaatg atatcgagac tgaggcaaga aggtgtgaaa gtgatgacac tgattctgaa   960
ggctgtggtg agggaagtga tggtgtggaa ttccaagatg cctcacgagt cctggaccaa  1020
gacgatggct tcgaattcca gctaccaaaa catcaaaagt gtgcctgtca cttacttaac  1080
ctagtctcaa gcgttgatgc ccaaaaagct ctctcaaatg aacactacaa gaaactctac  1140
agatctgtct ttggcaaatg ccaagcttta tggaataaaa gcagccgatc ggctctagca  1200
gctgaagctg ttgaatcaga aagccggctt cagcttttaa ggccaaacca aacgcggtgg  1260
aattcaactt ttatggctgt tgacagaatt cttcaaattt gcaaagaagc aggagaaggc  1320
gcacttcgga atatatgcac ctctcttgag gttccaatgt ttaatccagc agaaatgctg  1380
ttcttgacag agtgggccaa cacaatgcgt ccagttgcaa aagtactcga catcttgcaa  1440
gcggaaacga atacacagct ggggtggctg ctgcctagtg tccatcagtt aagcttgaaa  1500
cttcagcgac tccaccattc tctcaggtac tgtgaccac ttgtggatgc cctacaacaa  1560
ggaatccaaa cacgattcaa gcatatgttt gaagatcctg agatcatagc agctgccatc  1620
cttctcccta aatttcggac ctcttggaca aatgatgaaa ccatcataaa acgaggcatg  1680
gactacatca gagtgcatct ggagcctttg gaccacaaga aggaattggc caacagttca  1740
tctgatgatg aagatttttt cgcttctttg aaaccgacaa cacatgaagc cagcaaagag  1800
ttggatggat atctggcctg tgtttcagac accagggagt ctctgctcac gtttcctgct  1860
```

-continued

```
atttgcagcc tctctatcaa gactaataca cctcttcccg catcggctgc ctgtgagagg    1920
cttttcagca ctgcaggatt gcttttcagc cccaaaagag ctaggcttga cactaacaat    1980
tttgagaatc agcttctact gaagttaaat ctgaggtttt acaactttga gtagcgtgta    2040
ctggcattag attgtctgtc ttatagtttg ataattaaat acaaacagtt ctaaagcagg    2100
ataaaacctt gtatgcattt catttaatgt tttttgagat taaaagctta aacaag        2156
```

<210> SEQ ID NO 2
<211> LENGTH: 649
<212> TYPE: PRT
<213> ORGANISM: Oryzias latipes

<400> SEQUENCE: 2

```
Met Glu Glu Val Cys Asp Ser Ser Ala Ala Ser Ser Thr Val Gln
  1               5                  10                  15

Asn Gln Pro Gln Asp Gln Glu His Pro Trp Pro Tyr Leu Arg Glu Phe
             20                  25                  30

Phe Ser Leu Ser Gly Val Asn Lys Asp Ser Phe Lys Met Lys Cys Val
         35                  40                  45

Leu Cys Leu Pro Leu Asn Lys Glu Ile Ser Ala Phe Lys Ser Ser Pro
     50                  55                  60

Ser Asn Leu Arg Lys His Ile Glu Arg Met His Pro Asn Tyr Leu Lys
 65                  70                  75                  80

Asn Tyr Ser Lys Leu Thr Ala Gln Lys Arg Lys Ile Gly Thr Ser Thr
                 85                  90                  95

His Ala Ser Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
```

```
            325                 330                 335
Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
            355                 360                 365

Ser Ala Leu Ala Ala Glu Ala Val Glu Ser Glu Ser Arg Leu Gln Leu
            370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
            435                 440                 445

Asp Ile Leu Gln Ala Glu Thr Asn Thr Gln Leu Gly Trp Leu Leu Pro
            450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
            500                 505                 510

Leu Leu Pro Lys Phe Arg Thr Ser Trp Thr Asn Asp Glu Thr Ile Ile
            515                 520                 525

Lys Arg Gly Met Asp Tyr Ile Arg Val His Leu Glu Pro Leu Asp His
530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
            595                 600                 605

Ala Cys Glu Arg Leu Phe Ser Thr Ala Gly Leu Leu Phe Ser Pro Lys
            610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645

<210> SEQ ID NO 3
<211> LENGTH: 196
<212> TYPE: PRT
<213> ORGANISM: Zea mays

<400> SEQUENCE: 3

Ile Asn Leu Ile Glu Pro Tyr Lys Tyr Asp Glu Val Val Ser Leu Lys
1               5                   10                  15

Lys Leu His Leu Ala Ile Ile Met His Glu Tyr Pro Phe Asn Ile Val
            20                  25                  30

Glu His Glu Tyr Phe Val Glu Phe Val Lys Ser Leu Arg Pro His Phe
        35                  40                  45
```

```
Pro Ile Lys Ser Arg Val Thr Ala Arg Lys Tyr Ile Met Asp Leu Tyr
    50                  55                  60

Leu Glu Glu Lys Glu Lys Leu Tyr Gly Lys Leu Lys Asp Val Gln Ser
65                  70                  75                  80

Arg Phe Ser Thr Thr Met Asp Met Trp Thr Ser Cys Gln Asn Lys Ser
                85                  90                  95

Tyr Met Cys Val Thr Ile His Trp Ile Asp Asp Trp Cys Leu Gln
            100                 105                 110

Lys Arg Ile Val Gly Phe Phe His Val Glu Gly Arg His Thr Gly Gln
        115                 120                 125

Arg Leu Ser Gln Thr Phe Thr Ala Ile Met Val Lys Trp Asn Ile Glu
    130                 135                 140

Lys Lys Leu Phe Ala Leu Ser Leu Asp Asn Ala Ser Ala Asn Glu Val
145                 150                 155                 160

Ala Val His Asp Ile Ile Glu Asp Leu Gln Asp Thr Asp Ser Asn Leu
                165                 170                 175

Val Cys Asp Gly Ala Phe Phe His Val Arg Cys Ala Cys His Ile Leu
            180                 185                 190

Asn Leu Val Ala
        195

<210> SEQ ID NO 4
<211> LENGTH: 14
<212> TYPE: DNA
<213> ORGANISM: Oryzias latipes

<400> SEQUENCE: 4
ggagttcttg accc                                                       14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggagttcttg acag                                                       14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctggttcttg accc                                                       14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggagttcttg accc                                                       14
```

-continued

```
<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggagttcttc ttgaccc                                                      17

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggagttctct tgaccc                                                       16

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gttttttttt tacatctcaa ctg                                               23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctcaactgat agtctaatca cac                                               23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgctgagctc tcttatatag aga                                               23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tatagagatg gctgttatac gag                                               23
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
aagtgacgtc aatgtgtttt cag     23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
gttttcagct catctgttca tta     23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
ttggtcagac atgttcattg     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
atgttcattg gtcctttgga     20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
atagctgaag ctgctctgat c     21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
ctgctctgat catgaaacag     20

<210> SEQ ID NO 20

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcttaataaa gaaatatcgg cc                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aatatcggcc ttcaaaagtt cg                                              22

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgtaatcag agagtgtatg tgta                                            24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attgttacat ttattgcata caat                                            24

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctcaatatgc ttccttagg                                                  19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cttccttagg tttgatggcg                                                 20

<210> SEQ ID NO 26
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctactacat ggtgccattc ct                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cactgccaga tctgctgggc tt                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tccacccatg cttccagcag ta                                              22

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgttgtggtt gcaatccatt caac                                            24
```